United States Patent [19]

Inchauspé

[11]  4,344,889
[45]  Aug. 17, 1982

[54] PROCESS FOR THE CONTINUOUS PREPARATION OF SULFONATES DERIVED FROM MOLECULES HAVING LONG ALKYL CHAINS AND, MORE PARTICULARLY, SULFONATES DERIVED FROM FATTY ESTERS

[75] Inventor: Nicolas Inchauspé, Arthez de Bearn, France

[73] Assignee: Dumas et Inchauspé, Pau, France

[21] Appl. No.: 223,750

[22] Filed: Jan. 9, 1981

[30] Foreign Application Priority Data

Jan. 10, 1980 [FR] France ................................ 80 00521

[51] Int. Cl.³ ........................ C07C 143/90; C11D 1/28
[52] U.S. Cl. .................................................... 260/400
[58] Field of Search ......................................... 260/400

[56] References Cited

U.S. PATENT DOCUMENTS 2,863,887 12/1958 Beches .................................. 260/400
3,083,146 11/1958 Sweeney et al. ....................... 203/38
3,225,086 4/1963 Sias et al. ........................ 260/504 S
3,424,770 1/1969 Stein ..................................... 260/400

FOREIGN PATENT DOCUMENTS 907053 3/1954 Fed. Rep. of Germany .
672736 5/1952 United Kingdom .

OTHER PUBLICATIONS

"JOACS" by Stein and Baumann, vol. 52, pp. 323, 329 (1975).
"JOACS", by Kapur, Solomon and Bluestein, vol. 55, p. 549 (1978).
"Neftekhimiha", vol. 15, No. 5, pp. 760–762 (1975).

Primary Examiner—John F. Niebling
Attorney, Agent, or Firm—Fleit & Jacobson

[57] ABSTRACT

The starting material is subjected to the action of a sulfonating agent; the sulfonation product so obtained is degassed (2) and treated with slightly aqueous methanol in order to obtain, on the one hand, an ester phase containing the unsulfonated starting material which is returned to the sulfonation stage and, on the other hand, a methanol phase which contains the desired sulfonic acids and which is subjected to evaporation permitting the separation of the methanol from the said sulfonic acids.

9 Claims, 1 Drawing Figure

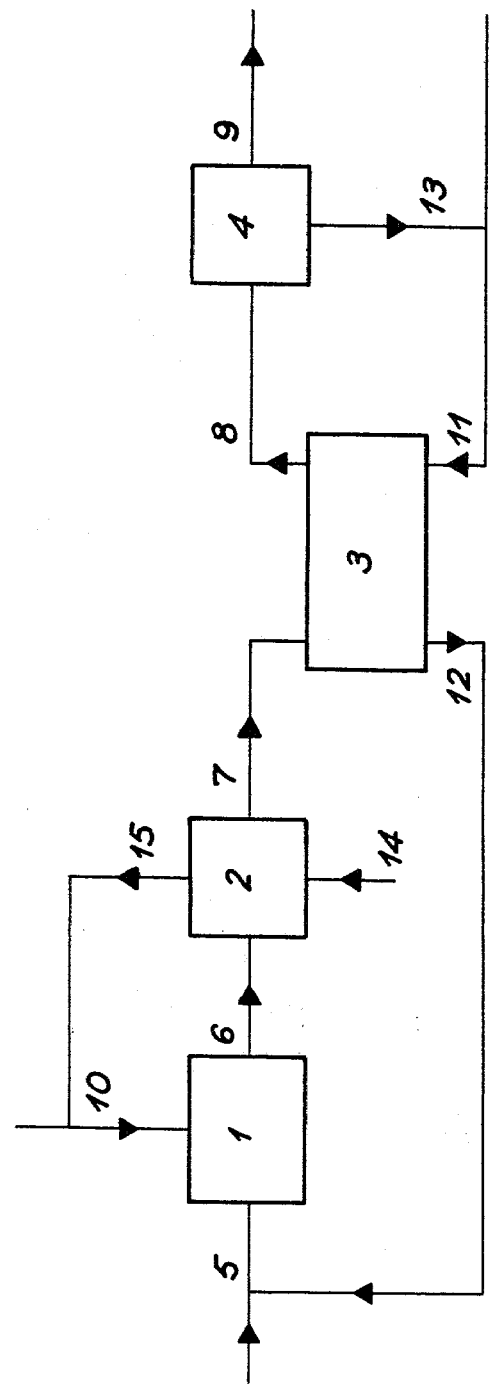

PROCESS FOR THE CONTINUOUS PREPARATION OF SULFONATES DERIVED FROM MOLECULES HAVING LONG ALKYL CHAINS AND, MORE PARTICULARLY, SULFONATES DERIVED FROM FATTY ESTERS

The subject of the present invention is a process for the continuous preparation of sulfonates derived from molecules having long alkyl chains, that is to say containing at least 11 $CH_2$ groups, and the products so obtained. The invention relates more particularly to the sulfonation of fatty esters. The term "fatty esters" is used to denote, especially, saturated alkyl esters of natural origin, that is to say obtained from vegetable oils such as palm oil, soya oil or colza oil, or from animal fats such as tallow. Of course, the process of the invention can also be applied to synthetic fatty esters.

The products obtained according to the invention from fatty esters are particularly valuable as surfactants because they are biodegradable while having the same detergent properties as sulfonates obtained from petroleum fractions; in addition they have the property of sequestering calcium and the other divalent ions of water which means that it is possible to avoid the use of phosphates which is forbidden in many countries because of the risk of eutrophication.

Attempts have been made to sulfonate fatty esters by using the process of sulfonation by gaseous sulfuric anhydride $SO_3$ prepared in advance by the catalytic oxidation of sulfurous anhydride. This process, which is used industrially for the sulfonation of alkylaryls or α-olefins, does not, however, give satisfactory results when sulfonating fatty esters. In fact, the molecules of these esters contain only one slightly active carbon atom, the carbon atom in the α-position to the acid carbon atom, so that the fixing of $SO_3$, which is spontaneous, exothermic and total in the case of alkylaryls and α-olefins, is slow and incomplete in the case of sulfonated fatty esters. The difficulties encountered when sulfonating fatty esters with sulfuric anhydride are described in an article by Stein and Baumann in JOACS, vol. 52, pages 323-329 (1975) and in an article by Kapur, Solomon and Bluestein in JOACS, vol. 55, page 549 (1978).

Furthermore, it has been proposed in German Patent DT No. 907053 to sulfonate fatty acids and their derivatives using a mixture of sulfurous anhydride and oxygen under ultra-violet irradiation. According to this patent, notably methyl laurate is subjected to sulfo-oxidation in order to obtain a sulfonation product which is hydrolyzed, before filtering the unsulfonated lauric acid, and which can then be extracted with butanol before neutralizing with soda. In addition, the Russian researchers Nametkin et al. have published a laboratory study on the sulfo-oxidation of synthetic fatty esters (Neftekhimiya, vol. 15, No. 5, 1975, pages 760-762). These authors, who are evidently not concerned with defining an industrial process, extract the resulting acids using barium carbonate, and then barium sulfonate is passed through an ion exchange column to give sodium sulfonate.

Finally, in the field concerned with the extraction of sulfonic acids manufactured from mineral oils, methanol has been used either in pure form or in conjunction with water. Thus, U.S. Pat. No. 3,225,086, the methanol is added after the water in such a manner that the final proportions are 33% water and 66% methanol. This process cannot be used for fatty esters which would, of course, by hydrolyzed. In British Pat. No. 672,736, a first extraction is carried out using a mixture of methanol and water in which the proportion of water is greater than 20% (therefore danger of hydrolysis) and then sulfuric acid is eliminated by a low-boiling gasoline. Finally, in U.S. Pat. No. 3,083,146, the treatment using methanol is not an extraction of the sulfonation products but is applied to a pure acid phase in order to reduce the sulfuric acid content. In fact, these various processes are not aimed at extracting all the acids formed in the oil; they therefore involve only one single treatment which yields in the extracted phase a different acid composition from the composition obtained in the oil and is therefore not economically advantageous.

The applicants have now discovered according to the invention that it is possible to sulfonate continuously molecules having long alkyl chains, and especially fatty esters, by repeatedly extracting the sulfonated product using slightly aqueous methanol and by recirculating the unsulfonated product. This process is especially advantageous in the case of fatty esters.

In fact, when fatty esters are sulfonated by sulfuric anhydride or a mixture of sulfurous anhydride and oxygen under irradiation, it is found that the fraction of sulfonated esters is slight compared with the quantity of esters that has not reacted. In order to render industrially viable a process for the sulfonation of fatty esters it is therefore necessary either to provide several sulfonation reactors in series—this, however, involves expensive apparatus—, or to return unreacted esters to the sulfonation stage, which would require the provision of an appropriate extraction agent for the sulfonated esters.

Water cannot be used as the extraction agent because it hydrolyzes esters and, what is more, the hydrolysis is facilitated by the acidity of the medium. Moreover, this hydrolysis is readily observed on the product neutralized with soda which shows an IR absorption band at 1560 $cm^{-1}$ corresponding to sodium carboxylate. Also, pure methanol cannot be used because at temperatures of over 30° C., at which the process must be carried out, the methanol completely dissolves the fatty bodies. The applicants have, however, surprisingly discovered that slightly aqueous methanol is an excellent extraction agent.

In order to establish quantitatively the ester-extraction properties of the mixture of methanol and water, the miscibility of mixtures of fatty esters, methanol and water was investigated. For this purpose, a starting mixture of specific composition is agitated and the two phases obtained are separated after separation by decantation.

The composition of each phase is analysed by distillation in vacuo which entrains water and methanol, followed by chromatography which separates the water and methanol.

The results are listed in the following Tables:

TABLE I

Mixture of water, methanol and hydrogenated and methylated palm oil, % by weight of the constituents, at 35° C.

| in the methanol phase obtained after decantation | | | in the ester phase obtained after decantation | | |
|---|---|---|---|---|---|
| Ester | Methanol | water | Ester | Methanol | water |
| 25.8 | 73.1 | 1.2 | 69.5 | 29.9 | 0.6 |
| 11.5 | 83.2 | 5.4 | 83.4 | 16.6 | 0.1 |

TABLE I-continued

Mixture of water, methanol and hydrogenated and methylated palm oil, % by weight of the constituents, at 35° C.

| in the methanol phase obtained after decantation | | | in the ester phase obtained after decantation | | |
|---|---|---|---|---|---|
| Ester | Methanol | water | Ester | Methanol | water |
| 6.2 | 84.8 | 9 | 89.4 | 10.5 | 0.2 |
| 3.8 | 79.1 | 17.2 | 96.2 | 3.7 | 0.1 |

TABLE II

Mixture of water, methanol and hydrogenated and methylated tallow, % by weight of the constituents, at 35° C.

| Methanol phase | | | Ester phase | | |
|---|---|---|---|---|---|
| Ester | Methanol | water | Ester | Methanol | water |
| 21.6 | 77.2 | 1.2 | 73.6 | 26.0 | 0.4 |
| 13.9 | 83.0 | 3.1 | 80.1 | 19.8 | 0.1 |
| 8.1 | 82.8 | 9.1 | 88.3 | 11.5 | 0.2 |
| 4.5 | 76.9 | 18.6 | 92.8 | 7.2 | 0.1 |

These Tables clearly show that, under the action of a small quantity of water (between a total of 1 and 3% by weight), the initially homogeneous mixture of methanol and esters separates into two phases one of which contains predominantly methanol and the other predominantly esters. It is also clear that the water is found almost entirely in the methanol phase; the whole process accordingly takes place as if the ternary mixture of esters, methanol and water behaved like a binary mixture of two sparingly soluble liquids: esters and aqueous methanol.

Tests for the extraction of acids were then carried out on mixtures obtained by photosulfonation and containing approximately 20% sulfonic acids and 80% unsulfonated esters. It should be noted that photosulfonation yields not only monosulfonic acids (mA) but also disulfonic acids (dA) and sulfuric acid ($SO_4$) in the average ratio of approximately 78/15/7% by weight. To determine the proportion of each of these acids, two well known analytical methods are used: titrimetry using methylene blue EPTON, and potentiometry in an anhydrous medium.

Table III below gives the significant results obtained for the extraction of sulfonic acids with aqueous methanol which characterizes the process of the invention. The initial mixture, denoted F, was extracted three times in succession according to the well known method of liquid/liquid co-current extraction, that is to say by adding pure aqueous methanol three times, firstly to F, secondly to the supernatant phase $R_1$ and thirdly to the resulting supernatant phase $R_2$ in order to obtain a final supernatant phase $R_3$ which contains practically no more sulfonic acids. After the first decantation an extract $E_1$ is obtained, after the second an extract $E_2$ and after the third an extract $E_3$. By mixing the three extracts a total extract $E_T$ is obtained which, after the evaporation of the methanol, gives a total dry extract $E_{Tdry}$. The mixtures before decantation into two phases are represented by $M_1$, $M_2$ and $M_3$. The density is represented by d. The acids taken together are represented by A and the unsulfonated fatty esters by FE.

In this Table and also hereinafter, the percentages indicated are by weight.

TABLE III

Extraction of sulfonic acids at 50° C. using slightly aqueous methanol

| Q | m(g) | % mA | % dA | % $SO_4$ | % A | % MW | % FE | mA(g) | dA(g) | $SO_4$(g) | MW(g) | FE(g) | d |
|---|---|---|---|---|---|---|---|---|---|---|---|---|---|
| F | 51.7 | 14 | 4 | 0.6 | 18.6 | 0 | 81.4 | 7.3 | 2.1 | 0.3 | 0 | 24.1 | 0.894 |
| $M_1$ | 55.6 | 13 | 3.8 | 0.6 | 17.4 | 7 | 75.6 | 7.3 | 2.1 | 0.3 | 3.9 | 42.1 | 0.890 |
| $R_1$ | 47.7 | 8.7 | 0.1 | 0.2 | 9 | 3.7 | 87.3 | 4.1 | 0 | 0.1 | 1.8 | 41.7 | 0.868 |
| $E_1$ | 7.9 | 39.4 | 26.1 | 2.8 | 68.3 | 26.9 | 4.8 | 3.1 | 2.1 | 0.2 | 2.1 | 0.4 | 1.014 |
| $M_2$ | 51.3 | 8.1 | 0.1 | 0.2 | 8.4 | 10.5 | 81.1 | 4.1 | 0 | 0.1 | 5.4 | 41.7 | 0.865 |
| $R_2$ | 46.5 | 4.9 | 0 | 0.1 | 5 | 7.2 | 87.8 | 2.3 | 0 | 0.1 | 3.4 | 40.9 | 0.862 |
| $E_2$ | 4.8 | 39.1 | 0.4 | 1.1 | 40.6 | 42.9 | 16.5 | 1.9 | 0 | 0.1 | 2 | 0.8 | 0.889 |
| $M_3$ | 50.2 | 4.5 | 0 | 0.1 | 4.6 | 13.9 | 81.5 | 2.3 | 0 | 0.1 | 7 | 40.9 | 0.859 |
| $R_3$ | 44.9 | 1.9 | 0 | 0 | 1.9 | 8.1 | 90 | 0.9 | 0 | 0 | 3.6 | 40.4 | 0.859 |
| $E_3$ | 5.3 | 26 | 0 | 0.6 | 26.6 | 63.3 | 10.1 | 1.4 | 0 | 0 | 3.3 | 0.5 | 0.864 |
| $E_T$ | 18 | 35.4 | 11.6 | 1.7 | 48.7 | 41.8 | 9.5 | 6.4 | 2.1 | 0.3 | 7.5 | 1.7 | 0.937 |
| $E_{Tdry}$ | 10.5 | 60.9 | 20 | 2.9 | 83.8 | 0 | 16.2 | 6.4 | 2.1 | 0.3 | 0 | 1.7 | 1.021 |

This Table shows that the final product $E_T$ obtained by mixing the three extracts $E_1$, $E_2$ and $E_3$ has an acid composition very similar to the initial composition of the photosulfonated mixture and that, after the evaporation of the methanol, this product contains approximately 84% total acid and 16% unsulfonated acid while the initial photosulfonated mixture contained 18% total acid and approximately 82% unsulfonated acid.

It is clear that several extraction stages are necessary since the disulfonic acid is more soluble than the others and passes completely into the methanolic phase on the first extraction, thereby yielding a first extract rich in disulfonic acid, which is not generally desirable.

Similar, and even better, results can be obtained by the known technique of countercurrent extraction.

The final product obtained is rust-colored and not black as is the case in the majority of the other sulfonation processes; it therefore does not require special bleaching treatment. The residual ester that it contains does not cause any problems since the product is subsequently neutralized to form a sulfonate and, in this same operation, the ester is converted into soap which contributes to the detergent power of the whole. The disulfonates have solubilizing properties similar to those of toluenesulfonates and the sodium sulfate represents a neutral charge in the formulation of the detergent.

The invention therefore relates to a continuous process for the sulfonation of molecules having long alkyl chains, characterized in that, after subjecting the starting material to the action of a sulfonating agent, the sulfonation product so obtained is extracted with slightly aqueous methanol in order to obtain, on the one hand, a phase containing the unsulfonated starting material which is returned to the sulfonation stage and, on the other hand, a methanol phase which is subjected to evaporation which permits the separation of, on the one hand, the methanol and, on the other hand, the sulfonic derivatives.

More particularly, the invention relates to a continuous process for the sulfonation of fatty esters, characterized in that, after subjecting a fatty ester, or a mixture of fatty esters (more especially a methyl ester or esters) to the action of a sulfonating agent, the sulfonation product so obtained is extracted repeatedly with slightly aqueous methanol in order to obtain, on the one hand, an ester phase containing the unsulfonated starting ester or esters which are returned to the sulfonation stage and, on the other hand, a methanol phase which contains the fatty acids and which is subjected to evaporation which permits the separation of, on the one hand, the methanol and, on the other hand, the sulfonic acids.

One form of process according to the invention will now be described, by way of example, with reference to the accompanying drawing, which is a diagrammatic representation of an apparatus suitable for carrying out the process of the invention.

Referring to the drawing, the fatty ester or mixture of fatty esters is introduced into the sulfonation reactor 1 via the pipe system 5. The sulfonating agent is introduced via the pipe system 10 into the reactor 1 where it is dispersed in the reaction medium by any suitable gas/liquid-injection means. The resulting sulfonation product, which contains, essentially, the sulfonated fraction of the starting ester and its unsulfonated complement, is drawn off continuously from the reactor and is fed via the pipe system 6 into a degassing unit 2 where a current of air, nitrogen or oxygen introduced via 14 eliminates the dissolved sulfonating agent which is returned to the reactor 1 via the pipe system 15. The degassed sulfonation product is fed via the pipe system 7 to an extractor 3 where the extraction solvent, that is to say, the slightly aqueous methanol, is introduced via the pipe system 11. The unsulfonated fatty ester (raffinate) discharged from the extractor is returned via the pipe system 12 to the reactor 1 while the extract containing the fatty acids and the methanol is fed via the pipe system 8 to a vaporizer 4. The methanol degassed by the vaporizer is returned via 13 to the extractor and the desired sulfonic acids are obtained at 9 at the outlet of the vaporizer.

The sulfonation is effected preferably by sulfo-oxidation under irradiation. For this purpose, a mixture of sulfurous anhydride and oxygen in an $SO_2/O_2$ ratio equal to or greater than 2, is introduced into the reactor 1 containing a lamp, for example a mercury lamp emitting UV rays of between 350 and 450 nm. The advantage of operating by sulfo-oxidation under irradiation is that the process can be carried out at temperatures below 40° C. which in turn avoids impairment of the product. The operation is generally carried out at a temperature of the order of 35° C. at which the fatty esters are liquid.

Alternatively, sulfuric anhydride may be used as the sulfonating agent.

According to the invention, for the extraction process a quantity of aqueous methanol is used that is preferably between half and double the quantity of sulfonation product on which this extraction is effected. The methanol used preferably contains a maximum of 20% and more particularly between 1 and 5% by weight of water.

This liquid/liquid extraction is carried out in several stages and preferably in at least three stages. Good results are obtained, for example, by co-current extraction in three stages or countercurrent extraction in five stages. The advantage of the countercurrent technique is that, although it is necessary to provide a greater number of stages, the quantities of aqueous methanol used are smaller.

As indicated above, the process of the invention can be applied to natural or synthetic fatty esters and, more particularly, to animal and vegetable oils and fats that have been hydrogenated and methylated. It is therefore possible to sulfonate according to the process of the invention commercial methyl stearate, hydrogenated and methylated tallow or hydrogenated and methylated palm oil. Commercial methyl stearate, having a melting point of 30° C., is virtually pure methyl stearate and corresponds fairly well to hydrogenated and methylated soya or colza oil (non-erucic). The hydrogenated and methylated commercial tallow, having a melting point of 27° C., comprises about 66% methyl stearate and 27% methyl palmitate, the remainder being made up of methyl myristate or esters having shorter chains. The hydrogenated and methylated commercial palm oil comprises about 60% methyl stearate and 40% methyl palmitate and may also contain up to 7 to 8% methyl laurate, for the same relative proportions of stearate/palmitate.

According to the invention, particularly advantageous results are obtained by using a starting material containing at least 90% methyl stearate and/or methyl palmitate or at least 90% hydrogenated and methylated tallow or hydrogenated and methylated palm oil.

It goes without saying that the embodiments that have just been described can be modified, notably by using other equivalent technical means, without exceeding the scope of the present invention.

I claim:

1. Process for the continuous preparation of sulfonic acids by sulfonating a starting material selected from the group consisting of methyl esters of fatty acids and mixtures thereof, which process comprises the steps of subjecting the said starting material to a sulfonation carried out by sulfo-oxidation under irradiation, degassing the product and extracting the sulfonic acids so obtained by repeated treatment with slightly aqueous methanol in order to obtain, on the one hand, a phase containing the unsulfonated starting material which is returned to the sulfonation step and, on the other hand, a phase which contains the sulfonic acids and which is subjected to evaporation in order to separate the methanol from the sulfonic acids, said extraction being performed at a temperature between 35° and 50° C.

2. Process according to claim 1, wherein the aqueous methanol used contains a maximum of 20 weight % water.

3. Process according to claim 1, wherein the aqueous methanol used contains from 1 to 5 weight % water.

4. Process according to claim 1, wherein the extraction using aqueous methanol is carried out in at least three stages.

5. Process according to claim 4, wherein the extraction is a co-current extraction.

6. Process according to claim 4, wherein the extraction is a counter-current extraction in five stages.

7. Process according to claim 1, wherein the sulfonating agent separated by degassing is returned to the sulfonation stage and the methanol separated by evaporation is returned to the stage where it is mixed with the sulfonation product.

8. Process according to claim 1, wherein the starting material comprises at least one ester of a saturated fatty acid.

9. Process according to claim 8, wherein a starting material is used which contains at least 90 weight % methyl stearate, palmitate or laurate or a mixture of such esters.

* * * * *